United States Patent

Dieter et al.

Patent Number: 5,384,330
Date of Patent: Jan. 24, 1995

[54] PHARMACEUTICALLY ACTIVE 1,2,4-TRIAMINO-BENZENE DERIVATIVES, PROCESSES FOR THEIR PREPARATION AND PHARMACEUTICAL COMPOSITIONS CONTAINING THEM

[75] Inventors: Hans-Reinhold Dieter, Darmstadt; Jurgen Engel, Alzenau; Bernhard Kutscher, Maintal; Emanuel Polymeropoulos, Frankfurt; Stefan Szelenyi, Schwaig; Bernd Nickel, Muhltal, all of Germany

[73] Assignee: Asta Medica Aktiengesellschaft, Germany

[21] Appl. No.: 2,458

[22] Filed: Jan. 8, 1993

[30] Foreign Application Priority Data

Jan. 8, 1992 [DE] Germany ............... 4200259

[51] Int. Cl.$^6$ ............................................. A61K 31/24
[52] U.S. Cl. ........................................ 514/535; 560/27
[58] Field of Search .......................... 560/27; 514/535

[56] References Cited

U.S. PATENT DOCUMENTS 5,091,581 2/1992 Seidel ................... 564/412

FOREIGN PATENT DOCUMENTS 0424194 9/1990 European Pat. Off. .
0452908 4/1991 European Pat. Off. .
3917113 11/1990 Germany .

OTHER PUBLICATIONS

German article entitled "Uber substituierte Polyaminopyridine" by Von Walter von Bebenburg et al. Chemiker Zeitung: Sonderdruck 103 (1979) 387–399 pp. 3–15.

*Primary Examiner*—José G. Dees
*Assistant Examiner*—Samuel Barts
*Attorney, Agent, or Firm*—Cushman, Darby & Cushman

[57] ABSTRACT

Pharmacologically active 1,2,4-triaminobenzene derivatives of the General Formula I:

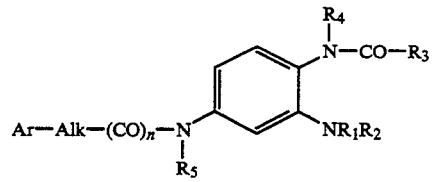

where the symbols R1' R2' R3' R4' R5' Ar and Alk have the following meanings:

where the symbols $R_1$, $R_2$, $R_3$, $R_4$, $R_5$, Ar and Alk have the following meanings:

$R_1$: hydrogen, $C_1$–$C_6$-alkyl, $C_2$–$C_6$-alkanoyl or the radical Ar;

$R_2$: hydrogen or $C_1$–$C_6$-alkyl;

$R_3$: $C_1$–$C_6$-alkoxy, $NH_2$, $C_1$–$C_6$-alkylamino, $C_1$–$C_6$-dialkylamino, amino substituted by the radical Ar, $C_1$–$C_6$-alkyl, $C_2$–$C_6$-alkenyl, $C_2$–$C_6$-alkynyl, the radical Ar or the radical ArO—;

$R_4$: hydrogen, $C_1$–$C_6$-alkyl or the radical Ar;

$R_5$: hydrogen or $C_1$–$C_6$-alkyl or the radical Ar;

Alk: a straight or branched alkylene group containing 1–9 carbon atoms, which can also be substituted by the radical Ar.

5 Claims, No Drawings

PHARMACEUTICALLY ACTIVE 1,2,4-TRIAMINO-BENZENE DERIVATIVES, PROCESSES FOR THEIR PREPARATION AND PHARMACEUTICAL COMPOSITIONS CONTAINING THEM

BACKGROUND OF THE INVENTION

In Chemiker Zeitung 103 (1979), pages 6–13 there is described a process for the preparation of 2-carbethoxyamino-5-(2,4,6-trimethylbenzylamino)aniline and of its hydrochloride (compound 81). There is no disclosure or teaching in this literature reference of any pharmacological activity of this compound.

SUMMARY OF THE INVENTION

It is an object of the present invention to provide compounds with favorable pharmacological properties which can for example be used as anti-epileptic, muscle-relaxing, fever-reducing and peripherally analgesically acting medications.

The compounds of the invention are pharmacologically active. In particular, the compounds of the invention have anticonvulsive, antipyretic and muscle-relaxant activity. In addition they also have a specific peripheral analgesic activity.

Preferred embodiments and details of the invention are described in more detail below:

It is an object of the present invention to provide 1,2,4-triaminobenzene derivatives of the General Formula I, i.e.:

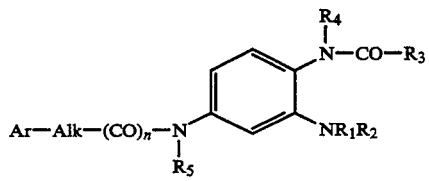

where the symbols $R_1$, $R_2$, $R_3$, $R_4$, $R_5$, Ar and Alk have the following meanings:

$R_1$: hydrogen, $C_1$–$C_6$-alkyl, $C_2$–$C_6$-alkanoyl or the radical Ar;

$R_2$: hydrogen or $C_1$–$C_6$-alkyl;

$R_3$: $C_1$–$C_6$-alkoxy, $NH_2$, $C_1$–$C_6$-alkylamino, $C_1$–$C_6$-dialkylamino, amino substituted by the radical Ar, $C_1$–$C_6$-alkyl, $C_2$–$C_6$-alkenyl, $C_2$–$C_6$-alkynyl, the radical Ar or the radical ArO—;

$R_4$: hydrogen, $C_1$–$C_6$-alkyl or the radical Ar;

$R_5$: hydrogen or $C_1$–$C_6$-alkyl or the radical Ar; Alk: a straight or branched alkylene group with 1–9 carbon atoms, which can also be substituted by the radical Ar;

Ar: a phenyl radical substituted by the radicals $R_6$, $R_7$ and/or $R_8$ where these radicals $R_6$, $R_7$ and $R_8$ are the same or different and represent $C_1$–$C_6$-alkyl, $C_3$–$C_7$-cycloalkyl, hydroxy, $C_1$–$C_6$-alkoxy, $C_2$–$C_6$-alkanoyloxy, halogen, hydroxy, $C_1$–$C_6$-halogenoalkyl, —CN, —$NH_2$, —NH—$C_1$–$C_6$-alkyl, —N($C_1$–$C_6$-alkyl)$_2$, —$CO_2$H, —CO—$C_1$–$C_6$-alkyl, —CO—O—$C_1$–$C_6$-alkyl, —COAr, —CO—OAr, —$CONH_2$, —CONH—$C_1$–$C_6$-alkyl, —CON($C_1$–$C_6$-alkyl)$_2$, —CONHAr, —NH—CO—$C_1$–$C_6$-alkyl, —NHCO—Ar, —NHCO—$C_1$–$C_6$-alkoxy, —NH—CO—OAr, —NHCO—$NH_2$, —NHCO—N(-$C_1$–$C_6$-alkyl)$_2$, —NHCO—NHAr, —NH—$SO_2$—$C_1$–$C_6$-alkyl, —NH—$SO_2$Ar, —NH—$SO_2$-nitrophenyl, —$SO_2$—OH, —$SO_2$—$C_1$–$C_6$-alkyl, —$SO_2$—Ar, —$SO_2$—$C_1$–$C_6$-alkoxy, —$SO_2$—OAr, —$SO_2$—$NH_2$, —$SO_2$—NH—$C_1$–$C_6$-alkyl, —$SO_2$—N($C_1$–$C_6$-alkyl)$_2$, —$SO_2$—NHAr, —$SO_2$—$C_1$–$C_6$-alkoxy;

n: or 1;

and pharmaceutically acceptable acid addition salts thereof, except for the compound 1-amino-2-carbethoxyamino-6-(2,4,6-trimethyl)-benzyl amino pyridine and the hydrochloride thereof.

It is a further object of the instant invention to provide a medication containing as active ingredient at least one 1,2,4-triaminobenzene derivative of the General Formula I, i.e.:

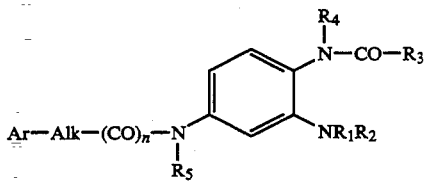

where the symbols $R_1$, $R_2$, $R_3$, $R_4$, $R_5$, Ar and Alk have the meanings given above and pharmaceutically acceptable acid addition salts thereof, together with a pharmaceutically-acceptable carrier such as, optionally, conventional auxiliary substances and carriers or diluents.

It is a further object of the invention to provide a process for the preparation of a medication characterized in that at least one compound of General Formula I including the compound 1-amino-2-carbethoxyamino-6-(2,4,6-trimethyl)benzylamino)-pyridine and its hydrochloride, is processed with conventional pharmaceutical carriers and/or diluents or other auxiliary substances into pharmaceutical formulations or brought into a therapeutically useful form.

It is a further object of the invention to provide compounds of formula I according to claim 1 including the compound 1-amino-2-carbethoxyamino-6-(2,4,6-trimethyl)benzylamino)-pyridine and its hydrochloride for the preparation of medications.

The alkyl groups, halogenalkyl groups, alkenyl groups, alkynyl groups, alkoxy groups, alkylamino groups, alkanoyl amino groups, alkanoyloxy groups and alkanoyl groups in general can be straight or branched. The same also applies to alkyl and alkyloxy groups (=alkoxy groups) if these are components of more complicated radicals for example in the form of a monoalkyl- or dialkylamino group, alkanoylamino group, carbalkoxy group, alkylcarbonyl group and analogous groups. The $C_3$–$C_7$-cycloalkyl group is preferably cyclopentyl or cyclohexyl. $C_2$–$C_6$-alkenyl preferably represents allyl. $C_2$–$C_6$-alkynyl preferably represents propargyl.

The halogen atoms are chlorine, bromine or fluorine, in particular chlorine or fluorine. The alkyl and alkoxy groups as such or as components of groups of more complicated radicals consist in particular of 1–4 carbon atoms, preferably 1 or 2 carbon atoms. Alkanoyl groups, such as alkanoylamino groups or alkanoyloxy groups consist in particular of 2–4, preferably 2–3 carbon atoms. Alk consists in particular of 1–3, preferably 1 or 2 carbon atoms.

Particularly favorable properties are displayed by those compounds of General Formula I where $R_1$ represents hydrogen, $C_1$–$C_6$-alkyl or $C_2$–$C_6$-alkanoyl, $R_2$ hydrogen or $C_1$–$C_6$-alkyl, $R_4$ and $R_5$ hydrogen, $R_3$ $C_1$–$C_6$-alkoxy, the alkylene group Alk is directly bound to the nitrogen atom (n=0) and represents $CH_2$ and Ar represents a halogenphenyl radical preferably fluorophenyl (for example 4-fluorophenyl) or a trifluoromethyl radical (for example 4-trifluoromethylphenyl).

Those compounds of General Formula I which contain asymmetrical carbon atoms and generally occur as racemates can be split into the optically active isomers in a manner known per se, for example using an optically active acid. It is, however, also possible to use an optically active starting material from the outset, the end product then being obtained in a correspondingly optically active or diastereomeric form. The present invention thus also comprises the D- and L-forms as well as the DL mixture in the event of the compound of General Formula I also contains an asymmetrical carbon atom and in the event of 2 and more asymmetrical carbon atoms also the corresponding diastereomeric forms.

Depending on the reaction conditions and on the starting materials, the end products of General Formula I are obtained in free form or in the form of their salts. The salts of the final products can be converted back into the bases in a manner known per se, for example with alkali or ion exchangers. Salts can be obtained from the latter by reaction with organic or inorganic acids, in particular those which are suitable for forming therapeutically useful salts.

The compounds of the invention are suitable for the preparation of pharmaceutical compositions. The pharmaceutical compositions or medications may contain one or more compounds of the invention. The conventional carriers and auxiliary substances can be used to prepare the pharmaceutical formulations.

The compounds of General Formula I can be prepared by two different processes, designated herein as process a) and process b).

In process a), the nitro group of a compound of General Formula II

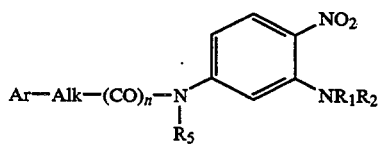

where $R_1$, $R_2$, $R_5$, Alk, Ar and n have the meanings given above or a compound of General Formula III, i.e.,

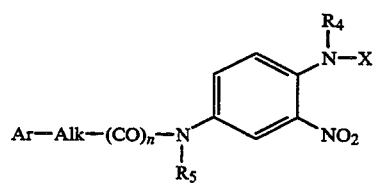

where X is hydrogen or the group —$COR_3$ and $R_3$, $R_4$, $R_5$, Alk, Ar and n have the meanings given above, is reduced to an amino group, the group —$COR_3$ is introduced by acylation if this is not present in the starting materials of General Formula II or III and the radical $R_1$, $R_2$, $R_4$ and $R_5$ are introduced optionally before or after introduction of the group —$COR_3$, In process b), a compound of General Formula IV, i.e.:

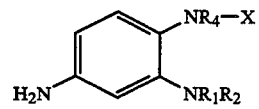

where X is hydrogen or the group —$COR_3$ and $R_1$, $R_2$, $R_3$ and $R_4$ have the meanings given above, is reacted with a compound of General Formula V, i.e.,

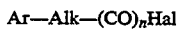

Ar—Alk—$(CO)_n$Hal      V where Ar, —Alk and n have the meanings given above and Hal is chlorine, bromine or iodine or a compound of General Formula VI, i.e., Ar—Alk'—CHO      VI where Ar has the meanings given above and Alk' is a straight or branched chain alkylene group having 0 to 8 carbon atoms or where Ar has branched alkylene group with 0–8 carbon atoms, where, when compound VI is used, the double bond of the Schiff's base obtained is reduced to the simple bond, the radicals —$COR_3$, R, $R_2$, $R_4$ and $R_5$ are introduced optionally by alkylation, arylation and/or acylation, the radical $R_3$ is optionally exchanged for another radical in the compounds obtained according to procedure a) or b) in the context of the definition given for $R_3$ and the compounds so obtained are converted into acid addition salts.

With regard to process a) (Reduction of the nitro group) catalytic hydrogenation has been found particularly suitable for reduction according to process a). The following catalysts may, for example, be used: Raney-nickel, precious metals such as palladium and platinum as well as compounds thereof, with and without carriers, such as for example barium sulphate, calcium sulphate and the like. It is advisable to carry out the hydrogenation of the nitro group at temperatures between 20° and 100° C. and a pressure of about 1 to 70 bar in solvent. Particularly suitable solvents are for example $C_1$–$C_4$-alkanols, $C_2$–$C_4$-diols and their lower alkyl ethers, cyclic ethers such as dioxane, tetrahydrofuran, methoxy ethanol, water, aromatic hydrocarbons (benzene, toluenes, xylenes) as well as mixtures of these agents. It may in some cases be of advantage for the subsequent isolation of the reduced compounds if drying agents such as anhydrous sodium or magnesium sulphate are added to the mixture to be hydrogenated at the outset.

The reduction may, however, also be carried out with nascent hydrogen for example zinc/hydrochloric acid, tin/hydrochloric acid, iron/hydrochloric acid or with salts of hydrogen sulfide in alcohol/water at about 70° to about 120° C. or with activated aluminum in aqueous ether at 20° to 40° C. or with tin II-chloride/-hydrochloric acid or with ammonium formate. If a starting material is used which contains an oxo group (for example alkyl carbonyl) it may be appropriate to protect this oxo group by conventional acetal formation (for example in the form of the ethylene acetal). This applies in particular to catalytic hydrogenation.

The reaction product obtained in this manner is usually immediately reacted in the reaction mixture obtained with a compound suitable for replacing a hydrogen atom of the amino group obtained by the reduction by the group —COR$_3$ without it being necessary to isolate the reduced compound. This applies in particular in the case of catalytic hydrogenation. The compound obtained by reduction of the nitro group can of course also be isolated and the —COR$_3$ group can then be introduced. Introduction of the —COR$_3$ group can be effected in the manner conventionally used for that purpose with conventional reagents, in particular halides of formula Hal—COR$_3$ (Hal=Cl, Br, I). Examples of such reagents are: C$_1$-C$_6$-alkylhaloformates (for example ethyl esters such as chlorine, bromine or iodo ethyl formates), -phenyl esters or Hal—CO—OAr. If R$_3$ is a C$_1$-C$_6$-alkyl group, acylating agents that may for example be considered are the halides (chlorine, bromine, iodine) or anhydrides of C$_1$-C$_6$-alkyne carboxylic acids, C$_2$-C$_6$-alkene carboxylic acids, C$_2$-C$_6$-alkyne carboxylic acids or acids of the formula ArCO$_2$H. It is also possible to use as acylating agents halides of the following formulae Hal—CO—NH$_2$, Hal—CO—NH—C$_1$-C$_6$-alkyl, Hal—CO—N(C$_1$-C$_6$-alkyl)$_2$ or Hal—CO—NHAr, if the radical R$_3$ has one of the given amine functions.

The latter compounds may, however, also be obtained in conventional manner from compounds of General Formula I where R$_3$ is C$_1$-C$_6$-alkoxy or phenoxy by reaction with ammonia, C$_1$-C$_6$-alkylamines, C$_1$-C$_6$-dialkylamines or amines NH$_2$—Ar.

These reactions preferably occur under pressure (10–50 bar) at temperatures between 0° and 220° C., preferably 100° to 200° C. in an inert solvent or dispersing agent. Agents of this kind that may for example be considered are: lower aliphatic alcohols (1–6 carbon atoms such as propanol, isopropanol, butanol, methoxyethanol), lower aliphatic ethers (diethyl ether, diisopropyl ether), aromatic hydrocarbons (benzene, toluene, xylene), cyclic ethers (dioxane, tetrahydrofuran), esters of lower aliphatic carboxylic acids with lower aliphatic alcohols, amides and N-alkyl-substituted amides of aliphatic C$_1$-C$_4$-carboxylic acids (dimethylformamide, dimethylacetamide), C$_1$-C$_6$-dialkylsulfones (dimethylsulfone, tetramethylenesulfone), C$_1$-C$_6$-dialkylsulfoxides (dimethylsulfoxide) as well as other aprotic agents such as n-methylpyrrolidone, tetramethylurea, hexamethylphosphoric acid triamide, acetonitrile as well as mixtures of these agents. This acylation may optionally also occur without the use of a solvent or dispersing agent. Without such an agent the reaction occurs for example between 0° and 200° C., preferably between 100° and 200° C.

Since the free amines of General Formula I where the group —COR$_3$ is hydrogen are sensitive to oxygen, a nitrogen atmosphere preferably is used.

In general the reaction components are reacted in molar amounts. It may, however, optionally be appropriate to use one reaction component in slight excess. The reaction may optionally be carried out in the presence of basic or acid-binding agents.

Agents of this kind that may for example be considered are: inorganic condensation agents such as ammonia, alkali metal or alkaline earth hydroxides, alkali metal- or alkaline earth carbonates or organic bases such as pyridine, tertiary amines (triethylamine), piperidine, alkali metal alcoholates, alkali metal acetates or also triethylphosphate. The alkali metals are in particular sodium or potassium. It is also possible to work under phase-transfer conditions i.e. with the addition of one or more long-chain amines such as a benzyl tributylammonium halide, a tetrabutyl ammonium halide or benzyl triphenyl phosphonium chloride.

Particularly when haloformates or derivatives thereof are employed, the basic condensation agents used may be tertiary amines, alkali metal hydroxides, alkali metal acetates or alkali metal bicarbonates.

The additionally available amino groups can for example contain a conventional amino protection group. Protection groups of this kind can be split by solvolysis or hydrogenolysis after completion of the reaction.

Starting materials of General Formula II or III may for example be obtained as follows.

1. By reacting a compound of general formula VII or VIII

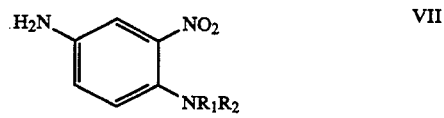

VII

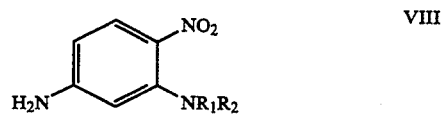

VIII with an aldehyde Ar—Alk'—CHO where Alk has the meanings given above and Alk' is a corresponding straight or branched alkylene group with 0–8 carbon atoms, reduction of the Schiff's base obtained in conventional manner and optionally introducing the radicals R$_1$, R$_2$ and R$_5$.

2. By acylating compounds of General Formula VII or VIII with a compound Ar—Alk—COHal, where Ar and Alk have the meanings given above and Hal represents chlorine, bromine or iodine and optionally introducing of the radicals R$_1$, R$_2$ and R$_5$.

It is also possible to obtain starting materials of General Formula II where n=0 (CO is absent) by reacting a compound of General Formula IX

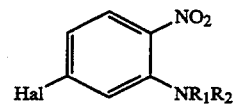

where Hal represents fluorine, chlorine or bromine, with an amine of the General Formula Ar—Alk—NH$_2$, where Ar and Alk have the meanings given, appropriately in the presence of a basic substance (tertiary amine) and optionally subsequent introduction of the radicals R$_1$, R$_2$ and R$_5$. Starting materials of General Formula III may for example also be obtained as follows:

A compound of general formula:

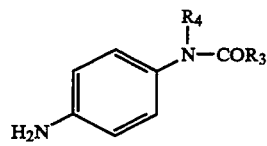

is reacted in conventional manner with phthalic acid anhydride (for example in glacial acetic acid at 90° C.), and the reaction product obtained, in which the free amino group in the 4-position is only protected by the phthalyl radical, is then nitrated in known manner in the 3-position to the phthalyl group, for example with fuming nitric acid in glacial acetic acid at 90°–100° C. The phthalyl radical is then split off in known manner (for example with hydrazine hydrate) in an inert agent such as 1,2-dimethoxyethane, a compound of the following formula being obtained:

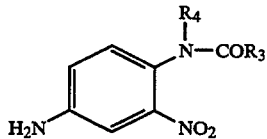

It is now possible to successively introduce the radicals Ar—Alk—$(CO)_n$— and $R_5$ in a conventional manner into the free amino group (for example as stated under procedure b) and optionally split off the radical —$COR_3$ in a known manner (replacement of —$COR_3$ by hydrogen).

The reactions described above for the preparation of the starting materials are carried out in conventional manner as described in Example 1 or by analogy thereto. The radicals $R_1$, $R_2$ and $R_5$ also are introduced in a conventional manner and as stated in the application (specification).

Process b) (reaction of a compound of general formula IV with a compound of general formula V or VI) is appropriately carried out at temperatures between 0° to 250° C., in particular 20° to 140° C.

Solvents or suspension agents that may for example be considered for the process are: water, aliphatic alcohols (ethanol, propanol, butanol), aromatic hydrocarbons (benzene, xylene, toluene), lower aliphatic acid amides (dimethylformamide), alicyclic and cyclically saturated ethers (diethyl ether, dioxane), N-methylpyrrolidone, dimethylsulfoxide, sulfolane, tetramethyl urea and mixtures of these agents.

Condensation agents that may be considered for process b) in the event of the reaction of a compound of General Formula IV with a compound of General Formula V are primarily for example sodium acetate, sodium amide, alkali metal carbonates and tertiary amines. Zinc chloride, phosphoroxychloride, p-toluenesulfonic acid, iodine and the like may also serve as condensation agents.

The process is carried out in the presence of hydrogen if a compound of General Formula VI is used. Catalysts that may be considered are conventional hydrogenation catalysts, preferably metallic hydrogenation catalysts such as Raney nickel, platinum, palladium. It is, however, also possible to use alkali metal borohydrides ($NaBH_4$) lithium borohydride, sodium cyanoborohydride.

Starting materials of General Formula IV may for example be obtained by conventional reduction of the corresponding nitro compounds (for example of General Formula VIII). This reduction may for example be carried out as in process a) and in the examples.

Starting materials of General Formula V or VI are known. Introduction of the radicals $R_1$, $R_2$, $R_4$ and $R_5$ including the group $COR_3$ according to process a) and/or b) is carried out in a conventional manner for example by the following reactions:

By alkylation or acylation: in this case particularly the acylation or alkylation of amino groups. The alkylation or acylation occurs for example by reaction with compounds of formulae R—Hal, $ArSO_2OR$ and $SO_2$-$(OR)_2$, where Hal is a halogen atom (in particular chlorine, bromine or iodine) and Ar is an aromatic radical (for example a phenyl or naphthyl radical optionally substituted by one or more lower alkyl radicals and R represents the radicals $C_1$-$C_6$-alkyl, Ar—$C_1$-$C_6$-alkyl, Ar—$C_1$-$C_6$-alkyl where the $C_1$-$C_6$-alkyl group contains a further radical Ar or represents Ar. Examples are p-toluenesulfonic acid-$C_1$-$C_6$-alkyl esters, $C_1$-$C_6$-dialkyl sulfates, $C_1$-$C_6$-alkyl halides and the like. In the previously mentioned compounds, the aryl group may in each case be substituted according to the meaning of Ar. The alkylation and or acylation reaction is optionally carried out with the addition of conventional acid-binding agents, such as alkali metal hydroxides, alkali metal carbonates, alkali metal hydrocarbonates, alkali metal hydrogen carbonates, alkaline earth carbonates, alkaline earth acetates, tertiary amines (for example trialkylamines such as triethylamine), pyridine or also alkali metal hydrides at temperatures between 0° and 200° C., preferably 40° and 140° C. in inert solvents or suspension agents. Solvents or dispersing agents that may be considered are for example: aromatic hydrocarbons such as benzene, toluene, xylene; aliphatic ketones such as acetone, methylethyl ketone; halogenated hydrocarbons such as chloroform, carbon tetrachloride, chlorobenzene, methylene chloride; aliphatic ethers such as butyl ether; cyclic ethers such as tetrahydrofuran, dioxane; sulfoxides such as dimethylsulfoxide; tertiary acid amides such as dimethyl formamide, N-methylpyrrolidone, hexamethylphosphoric acid triamide; aliphatic alcohols such as methanol, ethanol, isopropanol, amyl alcohol, tert.-butanol, cycloaliphatic hydrocarbons such as cyclohexane and the like. It is also possible to use aqueous mixtures of the solvents mentioned. The process is often carried out at the reflux temperature of the solvents or dispersing agents used. The alkylation reaction components are frequently used in excess. The alkylation can also be carried out in the presence of tetraalkylammonium salts (in particular the halides) in combination with alkali hydroxides at temperatures between 0°–100° C., preferably 20°–80° C., in an aprotic solvent or also in chloroform or methylene chloride. Aprotic solvents that may in particular be used are: tertiary amides (dimethylformamide, N-methyl-pyrrolidone, hexamethylphosphoric acid triamide), dimethylsulfoxide, acetonitrile, dimethoxyethane, acetone, tetrahydrofuran.

During acylation the amino groups for example have introduced in them the group —$COR_3$, the group —CO—$C_1$-$C_6$-alkyl, —CO—$C_2$-$C_6$-alkenyl, —CO—$C_2$-$C_6$-alkynyl, the $C_1$-$C_6$-alkoxycarbonyl group or the following groups: —COAr, —CO—OAr, —$CONH_2$ —CONH—$C_1$-$C_6$-alkyl, —CON($C_1$-$C_6$-alkyl)$_2$, —CONHAr, —$SO_2$—$C_1$-$C_6$-alkyl, —$SO_2$Ar, —$SO_2$-nitrophenyl.

The procedure is conducted in a manner known per se, for example using the corresponding acid halides (chloride, bromide) such as Carb-$C_1$-$C_6$-alkoxyhalide or corresponding anhydrides). The reaction temperatures are preferably between 20° and 120° C.

It is optionally also possible to carry out the alkylation and acylation by first preparing an alkali metal compound (sodium, potassium or also lithium salt for example) from the compound to be alkylated or acylated by reacting it in an inert solvent such as dioxane, dimethylformamide, benzene or toluene with an alkali metal, alkali metal hydride or alkali metal amide (in particular sodium or sodium compounds) or butyl lithium at temperatures between 0° and 150° C. and then adding the alkylating agent.

Instead of the alkylating and acylating agents listed, it is also possible to use other chemically equivalent agents conventionally used in chemistry, see for example also L. F. and Mary Fieser "Reagents for Organic Synthesis", John Wiley and Sons Inc., New York, 1967, Vol. 1, pages 1303–4 and Vol. 2, page 471.

Acyl groups present, such as Carb-$C_1$-$C_6$-alkoxy groups, $C_2$-$C_6$-alkanoyl groups and similar groups can be split off solvolytically. This splitting occurs in known manner, for example by saponification with acids (mineral acids such as hydrochloric acid, sulphuric acid, in particular concentrated hydrohalic acids such as HBr/glacial acetic acid) or using basic substances (potassium hydroxide, sodium hydroxide, aqueous alkali solutions, alcoholic alkali solutions, aqueous $NH_3$) at temperatures between 10° and 150° C., in particular 20°–100° C.

The compounds of the invention display a good anti-epileptic action for example in the maximal electro-cramp test (MES). For example in the above-mentioned test method, a dose of 6 mg/kg body weight, the rat shows a 50% inhibition of the cramps provoked by electric stimulation.

The minimum effective dose in the above-mentioned animal experiment is for example 2 mg/kg oral
0.5 mg/kg intravenous.

The general dose range that may for example be used for the effect (animal experiment as above) is:

2–20 mg/kg oral, in particular 10 mg/kg 0.5–5 mg/kg intravenous, in particular 2 mg/kg.

Generally speaking the activity of the compounds of the invention is comparable with the effect of the known medicinally active substance diazepam, although the compounds of the invention have a broader therapeutic spectrum.

The compounds of the invention may in particular be considered to be effective anti-epileptic agents.

Pharmaceutical formulations according to the invention contain in general between 10 to 100, preferably 30 to 60 mg of the active component(s) of the invention.

Administration may for example be in the form of tablets, capsules, pills, coated tablets, suppositories, ointments, gels, creams, powders, dusting powders, aerosols or in liquid form. Liquid application forms that may for example be considered are: oils or alcoholic or aqueous solutions as well as suspensions and emulsions. Preferred forms of application are tablets that contain between 30 and 60 mg or solutions that contain between 0.1 to 5 percent by weight of active substance.

A single dose of the active components of the invention can for example lie a) in the case of oral medicinal forms between 20 and 80 mg, preferably 30–60 mg
b) in the case of parenteral medicinal forms (for example intravenous, intramuscular) between 5–20 mg, preferably 8–16 mg.

(The doses are in each case related to the free base)

It is for example possible to recommend 3 times daily 1 to 3 tablets containing 30–60 mg of active substance or for example in the case of intravenous injection 1 to 3 times daily one ampoule of 3 to 5 ml content with 8 to 16 mg substance. In the case of oral administration, the minimum daily dose is for example 90 mg; the maximum daily dose in oral administration should not exceed 270 mg.

For the treatment of dogs and cats, the oral individual dose is generally between about 2 and 20 mg/kg body weight; the parenteral dose about between 1 and 5 mg/kg body weight.

The medication can be used in human medicine, in veterinary medicine and in agriculture, alone or mixed with other pharmacologically active substances.

DETAILED DESCRIPTION OF PREFERRED EMBODIMENT

The invention is illustrated by the following examples.

EXAMPLE 1

2-Amino-4-(4-fluorobenzylamino)-1-ethoxycarbonylaminobenzene.

Variant A

A suspension of 5.2 g (20 mmol) 2-amino-5-(4-fluorobenzylamino)-nitrobenzene or 5.2 g (20 mmol) 2-amino-4-(4-fluorobenzylamino)-nitrobenzene in 100 ml dioxane is hydrogenated at 55°–60° C. under normal pressure in the presence of 2 g Raney nickel. When hydrogen uptake is completed the catalyst is filtered off under an inert gas and the filtrate is reacted with 3.2 g (25 mmol) diisopropylethylamine. A solution of 2.3 g (21 mmol) ethyl chloroformate in 15 ml dioxane is added dropwise to the solution obtained with stirring and under an inert gas atmosphere (for example nitrogen) at 10°–20° C. When all has been added, the mixture is then stirred for 1 hour at room temperature, and 10 ml 6N ethanolic hydrochloric acid is then added dropwise with stirring and ice cooling. A colorless solid material gradually crystallizes out. The mixture is then stirred for 2 more hours at room temperature and the precipitated product is suction filtered. After recrystallization from ethanol/ether 5.5 g (73 % of theory) of 2-amino-4(4-fluorobenzylamino)-1-ethoxycarbonylaminobenzene obtained as dihydrochloride in the form of colorless to slightly pink crystals. M.p. of the dihydrochloride 182°–186° C. Preparation of the starting materials. 2-Amino-5-(4-fluorobenzylamino)-nitrobenzene A solution of 25.9 g (100 mmol) 2-amino-5-(4-fluorobenzylidene amino)-nitrobenzene in 250 ml dioxane/methanol mixture (4:1) is reacted in portions with stirring with 5.7 g (150 mmol) sodium tetrahydroborate. When all has been added, the mixture is stirred at room temperature for 2 hours more, the reaction solution then being concentrated under a vacuum until dry. The remaining dark red residue is taken up in 100 ml water and the resulting suspension is extracted four times with, in each case, 200 ml dichloromethane. The combined organic phases are dried with sodium sulfate and then concentrated in a vacuum. The remaining dark red oil is crystallized from 100 ml toluene. After drying in a vacuum, 21.0 g (80 % of theory) 2-amino-5-(4-fluorobenzylamino)-nitrobenzene are obtained as dark red crystals.

M.p. 111°–112° C.

2-Amino-5-(4-fluorobenzylideneamino)-nitrobenzene can for example be obtained as follows:

A solution of 15.3 g (100 mmol) 2-nitro-p-phenylenediamine and 13.6 g (110 mmol) 4-fluorobenzaldehyde in 400 ml xylene is heated under reflux in the presence of 0.5 g of an acid ion exchanger (for example Nafion) for 3 hours in a water separator. Insoluble constituents are filtered out hot and the mixture is allowed to stand overnight at room temperature. An orange-yellow solid crystallizes out. This solid is suction filtered, washed with a little toluene and dried in a vacuum. 22.0 g (85% of theory) 2-amino-5-(4-fluorobenzylideneamino)-nitrobenzene is obtained as orange-yellow crystals.

M.p. 136°–139° C.

2-Amino-4-(4-fluorobenzylideneamino)-nitrobenzene

A solution of 15.6 g (100 mmol) 2-amino-4-fluoronitrobenzene, 22.5 g (180 mmol) 4-fluorobenzylamine and 20.2 g (220 mmol) triethylamine in 150 ml dimethylsulfoxide is heated with stirring and under an inert gas atmosphere for 30 hours to 60°–70° C. When the reaction time is completed, the solvent is distilled off in a vacuum, the residue is taken up in 500 ml 0.5N hydrochloric acid and the mixture is stirred intensively at room temperature for 30 minutes. The precipitated solid is suction filtered and subjected to hot steam extraction with toluene. The product crystallizing out of the toluene after the mixture has been allowed to stand for twelve hours at 0°–4° C. is suction filtered and dried in a vacuum. 22.2 g (85 % of theory) are obtained. After being left to stand for 12 hours at 0°–4° C., 2-amino-4-(4-fluorobenzylamino)-nitrobenzene crystallizes out of the toluene phase as orange-yellow crystals.

M.p. 180° C.

Variant B

A suspension of 13.3 g (40 mmol) of 2-ethoxycarbonylamino-5-(4-fluorobenzylamino)-nitrobenzene in 150 ml 1,2-dimethoxyethane is hydrogenated at 55°–60° C. under normal pressure in the presence of 2 g Raney nickel. After hydrogen uptake has finished, the catalyst is filtered off under an inert gas and the filtrate is concentrated in a vacuum. The remaining reside is taken up in 150 ml ethanol, and 20 ml 6N ethanolic hydrochloric acid are added dropwise to the solution obtained under stirring and an inert gas atmosphere. After addition has finished the mixture is stirred for a further 1 hour, the precipitated solid is suction filtered and washed with ethanol. After drying in a vacuum 13.5 g (89% of theory) of the named compound are obtained as colorless to slightly pink crystals.

M.p. 186°–189° C.

Preparation of the starting substance

2-Ethoxycarbonylamino-5-(4-fluorobenzylamino)-nitrobenzene 39.8 g (120 mmol), 2-ethoxycarbonylamino-5(4-fluorobenzylidineamino)-nitrobenzene (prepared from 33.8 g (150 mmol) 5-amino-2-ethoxycarbonylamino-nitrobenzene and 19.2 g (155 mmol) 4-fluorobenzaldehyde) are reacted as stated above with 3.8 g (100 mmol) sodium tetrahydridoborate. After appropriate working up 31.3 g (78% of theory) 2-ethoxycarbonylamino-5-(4-fluorobenzylamino)nitrobenzene are obtained as dark red crystals.

M.p. 85°–87° C.

The 5-amino-2-ethoxycarbonylamino-nitro-benzene may for example be obtained as follows:

21.0 g (0.42 mol) hydrazine hydrate is added dropwise with stirring under reflux to a suspension of 142.1 g (0.4 mol) 2-ethoxycarbonylamino-5-phthalimido-nitrobenzene in 700 ml 1,2-dimethoxyethane and the mixture is allowed to react for a further 2 hours. After cooling to room temperature, precipitated phthalyl hydrazide is filtered off and the dark red filtrate in the vacuum is evaporated to dryness. The remaining solid residue is recrystallized from about 150 ml toluene. 84.4 g 5-amino-2-ethoxycarbonylaminonitrobenzene are obtained as dark red crystals.

M.p. 105°–107° C.

2-Ethoxycarbonylamino-5-phthalimido-nitrobenzene is for example obtained as follows:

75.7 g phthalic acid anhydride are added in portions to a solution of 90.1 g (0.5 mol) N-ethoxycarbonyl-p-phenylene diamine in 1.5 l glacial acetic acid with stirring and an inert gas atmosphere at 90° C. When the addition is completed, the mixture is left to react for a further 60 minutes. 27.5 ml fuming nitric acid are then added dropwise to the resulting suspension and the mixture is allowed to continue to react for 2 hours at 100° C. After cooling to room temperature, the precipitated solid substance is filtered off and washed neutral several times with a total of 2.5 liters of water. After drying in a vacuum, 149.9 g of the phthalimido compound are obtained as yellow crystals. M.p. 215°–216° C.

EXAMPLE 2

2-Amino-4-(4-trifluoromethylbenzylamino)-1-ethoxycarbonylamino-benzene

Variant A

A suspension of 9.3 g (30 mmol) 2-amino-5-(4-trifluoromethylbenzylamino)-nitrobenzene is hydrogenated in an analogous manner to Example 1 (variant A) and then reacted with 3.4 g (31 mmol) ethyl chloroformate. 5.8 g (45% of theory) of the above-mentioned end product is obtained as dihydrochloride in the form of colorless to weakly pink crystals. M.p. 159°–162° C.

Variant B

A suspension of 65.2 g (170 mmol) 2-ethoxycarbonylamino-5-(4-trifluoromethylbenzylamino)-nitro benzene is hydrogenated in a manner analogous to Example 1 (Variant B) and worked up appropriately. 52.2 g (72% of theory) of the above mentioned end product are obtained as dihydrochloride in the form of colorless crystals.

M.p. 160°–162° C.

The corresponding starting materials are prepared as described in Example 1 in analogous manner.

EXAMPLE 3

2-Amino-4-benzylamino-1-ethoxycarbonylamino-benzene

A suspension of 12.6 g (40 mmol) 5-benzylamino-2-ethoxycarbonyl-amino-nitrobenzene is hydrogenated by analogy with Example 1 (variant B) and worked up appropriately. 52.2 g (72% of theory) of the end product are obtained: colorless to pale pink crystals.

M.p. 178°–181° C.

EXAMPLE 4

2-Amino-4-(3,5-dichlorobenzylamino)-1-ethoxycarbonylamino benzene

A suspension of 15.5 g (50 mmol) 2-amino-5-(3,5-dichlorobenzylamino)-nitrobenzene is hydrogenated in a manner analogous with Example 1 (variant A) and worked up appropriately with 5.5 g (51 mmol) ethyl chloroformate. 10.8 g (51% of theory) of the end product are obtained as dihydrochloride: colorless to pale pink crystals. M.p. 134°–136° C.

EXAMPLE 5

2-Amino-4-(3,5-dichlorobenzylamino)-1-propyloxycarbonylamino benzene

A suspension of 15.5 g (50 mmol) 2-amino-5-(3,5-dichlorobenzylamino)-nitrobenzene is hydrogenated in a manner analogous with Example 1 (variant A) and worked up appropriately with 6.2 g (51 mmol) propyl chloroformate. 10.8 g of the end product are obtained in the form of the dihydrochloride. This forms colorless to pale pink crystals.

M.p. 154°–155° C.

EXAMPLE 6

2-Amino-4-(2-chlorobenzylamino)-1-(diethylcarbamoylamino) benzene

A suspension of 8.3 g (30 mmol) 2-amino-5-(2-chlorobenzylamino)-nitrobenzene is hydrogenated in a manner analogous with Example 1 (variant A) and worked up appropriately with 4.2 g (31 mmol) N,N-dimethylcarbamoyl chloride. 6.5 g of the end product are obtained as colorless to pale pink crystals.

M.p. 153°–155° C.

EXAMPLE 7

2-Amino-4-(2,4-dichlorobenzylamino)-1-(dimethylcarbamoylamino) benzene

A suspension of 31.2 g (100 mmol) 2-amino-5-(2,4-dichlorobenzylamino)-nitrobenzene is hydrogenated in a manner analogous with Example 1 (variant A) and worked up appropriately with 13.9 g (101 mmol) N,N-dimethylcarbamoyl chloride. 12.4 g of the end product are obtained in the form of the dihydrochloride. This forms colorless to pale pink crystals.

M.p. 147°–152° C.

EXAMPLE 8

1,2-Diacetylamino-4-(4-fluorobenzylamino) benzene 9.4 g (30 mmol) 4-(4-fluorobenzylideneamino)-N,N'-diacetyl-o-phenylene diamine are reduced in 250 ml dioxane/methanol mixture (4:1) as described in Example 1 with 0.9 g (25 mmol) sodium tehrahydriodoborate. The free base obtained is then transferred into the hydrochloride directly with alcoholic hydrochloric acid. 7.2 g of the end product are obtained in the form of the monohydrochloride. This forms colorless crystals.

M.p. 165°–168° C.

4-(4-Fluorobenzylideneamino)-N,N'-diacetyl-o-phenylene diamine is for example obtained by reacting 8.3 g (40 mmol) 4-amino-N,N'-diacetyl-o-phenylene diamine with 5.1 g (41 mmol) 4-fluorobenzaldehyde (as described in Example 1). Yield: 11.0 g yellow crystals.

M.p. 152°–156° C.

What is claimed is:

1. A compound selected from the group consisting of 2-amino-4-(4-fluorobenzylamino)-1-ethoxycarbonylaminobenzene and 2-amino-4-(4-trifluoromethylbenzylamino)-1-ethoxycarbonylamino benzene, and pharmaceutically acceptable acid addition salts thereof.

2. A pharmaceutical composition comprising an effective amount of the compound of claim 1 and a pharmaceutically acceptable carrier therefor.

3. A method of producing an anti-eleptic, muscle relaxing, fever reducing, peripherally analgesic or anti-convulsive effect in a patient in need thereof which comprises administering an effective amount of a pharmaceutical composition as set forth in claim 2.

4. A compound selected from the group consisting of 2-amino-4-(4-fluorobenzylamino)-1-ethoxycarbonylaminobenzene and pharmaceutically acceptable acid addition salts thereof.

5. A compound selected from the group consisting of 2-amino-4-(4-trifluoromethylbenzylamino)-1-ethoxycarbonylamino benzene and pharmaceutically acceptable acid addition salts thereof.

* * * * *